United States Patent [19]

Hayashida et al.

[11] Patent Number: 5,428,152

[45] Date of Patent: * Jun. 27, 1995

[54] BIS(TRIALKYLSILOXY)SILICON NAPHTHALOCYANINE COMPOUNDS WHEREIN ALL THE ALKYL GROUPS ARE THE SAME AND HAVE 1-3 CARBON ATOMS

[75] Inventors: Shigeru Hayashida; Seiji Tai, both of Hitachi, Japan

[73] Assignee: Hitachi Chemical Company, Ltd., Tokyo, Japan

[*] Notice: The portion of the term of this patent subsequent to Jan. 14, 2009 has been disclaimed.

[21] Appl. No.: 74,975

[22] Filed: Jun. 10, 1993

Related U.S. Application Data

[60] Continuation of Ser. No. 770,360, Oct. 3, 1991, abandoned, which is a division of Ser. No. 348,128, May 3, 1989, Pat. No. 5,081,236, which is a continuation of Ser. No. 149,559, Jan. 28, 1988, abandoned, which is a division of Ser. No. 41,409, Apr. 23, 1987, Pat. No. 4,749,637.

[30] Foreign Application Priority Data

Apr. 24, 1986 [JP] Japan .................. 61-95337
Jun. 26, 1986 [JP] Japan .................. 61-150126

[51] Int. Cl.⁶ .................. C07D 209/56; G03C 1/72
[52] U.S. Cl. .................. 540/128; 430/78
[58] Field of Search .................. 540/128; 430/78

[56] References Cited

U.S. PATENT DOCUMENTS 4,725,525 2/1988 Kenney et al. .................. 430/270
5,081,236 1/1992 Hayashida et al. .................. 540/128

*Primary Examiner*—Munkund J. Shah
*Assistant Examiner*—Pavanaram K. Sripada
*Attorney, Agent, or Firm*—Antonelli, Terry, Stout & Kraus

[57] ABSTRACT

Disclosed are naphthalocyanine compounds having siloxy groups bonded to a central metal silicon. The compounds can be used as a charge generating substance of an electrophotographic plate having high sensitivity to the longer wavelength light of about 800 nm without conducting a special treatment. The naphthalocyanine compounds are represented by the formula:

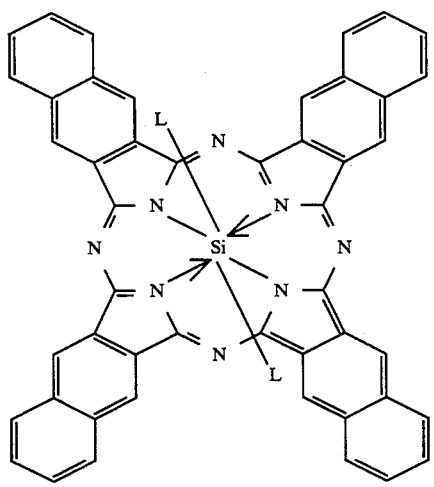

wherein L is a group of the formula $R_1R_2R_3SiO-$, and $R_1$, $R_2$ and $R_3$ are each a same alkyl group having 1-3 carbon atoms.

5 Claims, 7 Drawing Sheets

BIS(TRIALKYLSILOXY)SILICON NAPHTHALOCYANINE COMPOUNDS WHEREIN ALL THE ALKYL GROUPS ARE THE SAME AND HAVE 1-3 CARBON ATOMS

This application is a continuation of application Ser. No. 07/770,360, filed on Oct. 3, 1991, abandoned, which is a divisional of application Ser. No. 07/348,128, filed on May 3, 1989, now U.S. Pat. No. 5,081,236, which is a continuation application of application Ser. No. 07/149,559, filed Jan. 28, 1988, now abandoned, which is a divisional application of application Ser. No. 07/041,409, filed Apr. 23, 1987, now U.S. Pat. No. 4,749,637.

BACKGROUND OF THE INVENTION

This invention relates to an electrophotographic plate having high sensitivity for a long wavelength light of about 800 nm which is in a diode laser region.

Electrophotographic plates have been produced by forming a selenium (Se) film of about 50 μm thick on an electroconductive substrate made of, for example, aluminum, by a vacuum deposition method. But the Se plate has a problem in that it has sensitivity only upto a wavelength of near 500 nm. On the other hand, there have been known electrophotographic plates produced by forming a Se layer of about 50 μm on an electroconductive substrate, followed by the formation of a selenium-tellurium (Se—Te) alloy layer of several μm thick. Such electrophotographic plates can extend the spectral light-sensitivity to a longer wavelength side by making the Te content in the Se—Te alloy higher. But with an increase of the Te adding amount, the surface charge retention properties of such electrophotographic plates become worse and cannot be used practically as an electrophotographic plate: this is a serious problem.

It is also known so-called complex double layer type electrophotographic plates produced by forming a charge generation layer on an aluminum substrate by coating chlorocyan blue or squaraine derivative in about 1 μm thickness, and forming a change transport layer thereon by coasting a polyvinylcarbazole having high insulation resistance or a mixture of a pyrazoline derivative and polycarbonate in 10–20 μm thickness. But such electrophotographic plates have practically no sensitivity to a light having a wavelength of 700 nm or more. Further, it is also known electrophotographic plates improved in the defect of the complex double layer type mentioned above so as to have sensitivity in about 800 nm which is in the diode laser region. But many of them show the longer wavelength sensitivity by forming a thin film with about 1 μm film thickness of a metal phthalocyanine having one or more metals of the group III or IV of the periodic table as center metals by a vacuum deposition method, and immersing the resulting thin film in a shifting agent solution or contacting the resulting thin film with a vapor of the shifting agent so as to shift the absorption of original about 700 nm to about 800 nm. On the thus treated thin film, a charge transport layer is formed by coating a polyvinylcarbazole having high insulation resistance or a mixture of a pyrazoline derivative or a hydrazone derivative and a polycarbonate resin or polyester reins in 10–20 μm thickness to produce complex double layer type electrophotographic plates. But in this case, since the metal phthalocyanine thin film having the metals of the group III or IV of the periodic table as center metals used as a charge generation layer has no absorption in the diode laser region of about 800 nm essentially, there is a serious problem in that such electrophotographic plates have no sensitivity or only low sensitivity to the light of about 800 nm (U.S. Pat. No. 4,426,434).

In laser beam printers using electrophotographic plates and laser beams as a light source, the use of diode laser as the light source has been tried variously in recent years. In this case, since the wavelength of this light source is about 800 nm, it is strongly desired to produce electrophotographic plates having high sensitivity to the longer wavelength light of about 800 nm.

SUMMARY OF THE INVENTION

It is an object of this invention to provide an electrophotographic plate having high sensitivity to the longer wavelength light of about 800 nm essentially without conducting special treatment.

This invention provides an electrophotographic plate comprising an electroconductive support and a photoconductive layer containing an organic photoconductive substance as a charge generating material formed on the support, said organic photoconductive substance being a naphthalocyanine compound represented by the formula;

(I)

wherein L is a group of the formula: $R_1R_2R_3Si—O—$; $R_1$, $R_2$ and $R_3$ are independently hydrogen, an alkyl group or an alkoxy group.

DESCRIPTION OF THE PREFERRED EMBODIMENTS

The naphthalocyanine compound of the formula:

(I)

wherein L is a group of the formula: $R_1R_2R_3Si$—O—; $R_1$, $R_2$ and $R_3$ are independently hydrogen, an alkyl group preferably having 1 to 12 carbon atoms, or an alkoxy group preferably having 1 to 12 carbon atoms, generates charge by irradiation of a light.

The naphthalocyanine compound of the formula (I) can be produced by reacting dihydroxy-silicon naphthalocyanine of the formula:

(II)

with a compound of the formula:

(III)

wherein $R_1$, $R_2$, and $R_3$ are as defined above; and X is a hydroxyl group or a halogen with heating.

In this case, the reaction temperature is preferably from 150° to 200° C. Further, it is preferable to use an organic solvent such as tetralin, chlorobenzene, quinoline, 1-chloronaphthalene, 1,2,4-trimethylbenzene, 1,2,3-trimethylbenzene, xylene, toluene, benzene, dichlorobenzene, β-picoline, etc. alone or as a mixture thereof. Further, when X is a halogen in the compound of the formula (III), it is preferable to use a catalyst such as tri-n-butylamine, tri-n-propylamine, tri-n-hexylamine, pyridine, or the like base. The catalyst is preferably used in an amount of 0.1 to 1% by weight based on the weight of dihydroxysilicon naphthalocyanine.

In the production of bis(triethylsiloxy)silicon naphthalocyanine, it is better to use triethylsilanol than to use triethylchlorosilicon considering the yield.

Separation and purification of the bis(trialkylsiloxy)silicon naphthalocyanine from the reaction mixture can be carried out by a method comprising concentrating the reaction mixture, drying it and recrystallizing it, or a method wherein the reaction mixture is poured into a poor solvent for the above-mentioned naphthalocyanine such as water, methanol, ethanol, propanol, or the like alcohol, a produced precipitate is collected and subjected to recrystallization, or the like.

The recrystallization can be carried out by using the above-mentioned aromatic solvent or halogen series solvent.

Dihydroxysilicon naphthalocyanine is a known compound and can be produced, for example, by the method described in J. Am. Chem. Soc. vol. 106, pp 7404-(1984) and the route (A) as shown below:

That is, α, α, α', α'-tetrabromo-o-xylene [the formula (V)] in an amount of 0.1 mol and fumaronitrile in an amount of 0.178 mol are reacted at 75° C. for 7 hours in the presence of 0.67 mol of sodium iodide in anhydrous N,N-dimethylformamide to yield 2,3-dicyanonaphthalene of the formula (VI). Subsequently, 57.3 mmol of the 2,3-dicyanonaphthalene is reacted with ammonia in the presence of sodium methoxide in methanol with heating for 3 hours to yield 1,3-diiminobenzo(f)isoindoline of the formula (VII). Further, 30.6 mmol of the 1,3-diiminobenzo(f)-isoindoline was reacted with 47.1 mmol of silicon tetrachloride in anhydrous tetralin and anhydrous tri-n-butylamine under reflux for about 3 hours to give dichlorosilicon naphthalocyanine [SiNcX₂(X=Cl)] which can be represented by the formula (II) except that the two OHs are replaced by two Cl's. Then, this compound is treated with concentrated sulfuric acid and then concentrated ammonia water to give dihydroxysilicon naphthalocyanine [SiNcX₂(X=OH)] of the formula (II).

The dihydroxysilicon naphthalocyanine of the formula (II) is reacted with a compound of the formula (III), for example, a chlorosilane compound of the formula:

$$R_1R_2R_3SiCl \qquad (III')$$

wherein $R_1$, $R_2$ and $R_3$ are as defined above, at 140° to 150° C. for 1.0 to 3.0 hours, e.g. 1.5 hours to yield the naphthalocyanine compound of the formula (I) wherein the two siloxy groups of the formula: $R_1R_2R_3Si$—O— are bonded to the central metal silicon.

Examples of the siloxy group of the formula: $R_1R_2R_3Si$—O— are a dimethylsiloxy group, a trimethylsiloxy group, a dimethoxymethylsiloxy group, a dimethylpropylsiloxy group, a t-butyldimethylsiloxy group, a triethylsiloxy group, a triethoxysiloxy group, a tripropylsiloxy group, a dimethyloctylsilxoy group, a tributylsiloxy group, a trihexylsiloxy group, etc.

The electrophotographic plate of this invention is produced by forming a photoconductive layer on an electroconductive support.

The photoconductive layer is a layer containing an organic photoconductive substance, and can be in the form of a film of an organic photoconductive substance, a film containing an organic photoconductive substance, and a binder, a complex type film comprising a charge generation layer and a charge transport layer, etc.

As the organic photoconductive substance, the naphthalocyanine of the formula (I) is used as an essential component. It is possible to co-use one or more conventional photoconductive substances. It is preferable to use the naphthalocyanine of the formula (I) alone or in combination with one or more organic pigments generating charge together with one or more charge transport substances. In the above-mentioned charge generation layer, the naphthalocyanine of the formula (I) and the organic pigments generating charge are contained, and in the charge transport layer, the charge transport substances are contained.

As the organic pigment which is included in the charge generation layer for charge generation, there can be used azoxybenzenes, disazos, trisazos, benzimidazoles, multi-ring quinones, indigoids, quinacridones, metallic or non-metallic phthalocyanines having various crystal structures, perylenes, methines, etc., these pigments being known for charge generation. These pigments can be used alone or as a mixture thereof. These pigments are, for example, disclosed in British Patent Nos. 1,370,197, 1,337,222, 1,337,224 and 1,402,967, U.S. Pat. Nos. 3,887,366, 3,898,084, 3,824,099 and 4,028,102,, Canadian Patent No. 1,007,095, German Offenlegungschrift 2,260,540, etc. It is also possible to use all organic pigments which can generate charge carriers by illumination with light other than those mentioned above.

A part of typical examples of the organic pigments are illustrated below, but needless to say, the organic pigments are not limited thereto.

Examples of the phthalocyanine series pigments are copper phthalocyanine, metal free phthalocyanines, magnesium phthalocyanine, aluminum phthalocyanine, chromium phthalocyanine, copper-sulfated phthalocyanine, etc. As to their crystal forms, α-form, β-form, γ-form, ε-form, χ-form, etc., may be used. Particularly, the use of $\tau$, $\tau'$, $\eta$ and $\eta'$ type metal free phthalocyanines disclosed in U.S. Pat. No. 4,619,879, etc. is preferable.

As the charge transport substances, there can be used high polymeric compounds such as poly-N-vinylcarbazole, halogenated poly-N-vinylcarbazole, polyvinylpyrene, polyvinylindoloquinoxaline, polyvinylbenzothiophene, polyvinylanthracene, polyvinylacridine, polyvinylpyrazoline, etc., low molecular-weight compounds such as fluorenone, fluorene, 2,7-dinitro-9-fluorenone, 4H-indeno(1,2,6)thiophene-4-one, 3,7-dinitrodibenzothiophene-5-oxide, 1-bromopyrene, 2-phenylpyrene, carbazole, N-ethylcarbazole, 3-phenylcarbazole, 3-(N-methyl-N-phenylhydrazone)methyl-9-ethylcarbazole, 2-phenylindole, 2-phenylnaphthalene, oxadiazole, 2,5-bis(4-diethylaminophenyl)-1,3,4-oxadiazole, 1-phenyl-3-(4-diethylaminostyryl)-5-(4-diaminostyryl)-5-(4-diethylaminophenyl)pyrazoline, 1-phenyl-3-(p-diethylaminophenyl)pyrazoline, p-(dimethylamino)-stilbene, 2-(4-dipropylaminophenyl)-4-(4-dimethylaminophenyl)-5-(2-chlorophenyl-1,3-oxazole, 2-(4-dimethylaminophenyl)-4-(4-dimethylaminophenyl)-5-(2-fluorophenyl)-1,3-oxazole, 2-(4-diethylaminophenyl)-4-(4-dimethylaminophenyl)-5-(2-fluorophenyl)-1,3-oxazole, 2-(4-dipropylaminophenyl)-4-(4-dimethylaminophenyl)-5-(2-fluorophenyl)-1,3-oxazole, imidazole, chrysene, tetraphene, acridine, triphenylamine, and derivatives of these compounds.

When the naphthalocyanine compound of the formula (I) with or without the organic pigments which generate charge is used in admixture with the charge transport substances, it is preferable to mix the former/the latter in a weight ration of 10/1 to 2/1. When a high polymeric compound is used as the charge transport substance, the use of a binder is not always necessary. But in such a case or a low molecular-weight compound is used as the charge transport substance, it is preferable to use the binder in an amount of 30% by weight or more. Further, even if the charge transport substance is not used, the binder may be used in the same amount as mentioned above. When the binder is used, there can be used one or more additives such as plasticizers, flowability imparting agents, pin hole inhibiting agents, etc., depending on purposes.

When a complex type photoconductive layer comprising a charge generation layer and a charge transport layer is formed, the naphthalocyanine compound of the formula (I) with or without an organic pigment which can generates charge is contained in the charge generation layer which may contain the binder in an amount of 500% by weight or less based on the weight of the organic pigment, or contain the additives in an amount of 5% by weight or less based on the weight of the naphthalocyanine compound of the formula (I) or a total amount of the naphthalocyanine compound of the formula (I) and the organic pigment. The charge transport substance is contained in the charge transport layer which may contain the binder in an amount of 500% by weight or less based on the weight of the charge transport substance. When the low molecular-weight compound is used as the charge transport substance, it is preferable to contain the binder in an amount of 50% by weight or more based on the weight of the low molecular-weight compound. The charge transport layer may contain the above-mentioned additives in an amount of 5% by weight or less based on the weight of the charge transport substance.

As the binder which can be used in all the cases mentioned above, there can be used silicone resins, polyamide resins, polyurethane resins, polyester resins, epoxy resins, polyketone resins, polycarbonate resins, polyacrylic resins, polystyrene resins, styrene-butadiene copolymers, polymethyl methacrylate resins, polyvinyl chlorides, ethylene-vinyl acetate copolymers, vinyl chloride-vinyl acetate copolymers, polyacrylamide resins, polyvinylcarbazole, polyvinylpyrazoline, polyvinylpyrene, etc. It is also possible to use one or more thermosetting resins and photo-curable resins which are crosslinked by heat and/or light.

In any cases, there is no particular limitation to the resins, so long as they can form insulating films under normal conditions or can form films by curing with heat and/or light.

As the plasticizers, there can be used conventional ones such as halogenated paraffins, dimethyl naphthalene, dibutyl phthalate, etc. As the flowability imparting agents, there can be used conventional ones such as Modaflow (a trade name mfd. by Monsanto Chemical Co.), Akulonal 4F (a trade name mfd. by BASF AG.), etc. As the pin hole inhibiting agents, there can be used conventional ones such as benzoine, dimethyl phthalate, etc. These additives can be used depending on purposes in amounts suitable for purposes.

As the electroconductive support for forming an electroconductive layer, there can be used paper or plastic films subjected to the electroconductivity treatment, plastic films clad with a metal foil such as aluminum, metal plates, and the like.

The electrophotographic plate of this invention comprises an electroconductive support and a photoconductive layer formed thereon. The thickness of the photoconductive layer is preferably 5 to 50 $\mu$m. When the complex type comprising the charge generation layer and the charge transport layer is used as the photoconductive layer, the thickness of the charge generation layer is preferably 0.001 to 10 $\mu$m, more preferably 0.2 to 5 $\mu$m. When the thickness is less than 0.001 $\mu$m, it is difficult to form the charge generation layer uniformly, whereas when the thickness is more than 10 $\mu$m, there is a tendency to lower electrophotographic properties. The thickness of the charge transport layer is preferably 5 to 50 $\mu$m, more preferably 8 to 20 $\mu$m. When the thickness is less than 5 $\mu$m, the initial potential is lowered, whereas when the thickness is more than 50 $\mu$m, there is a tendency to lower the sensitivity.

The photoconductive layer can be formed on the electroconductive support by a vapor deposition method wherein an organic photoconductive substance is vapor deposited on the electroconductive support, or by a coating method wherein an organic photoconductive substance and other components depending on purposes are dissolved or dispersed uniformly in a solvent and coated on the electroconductive support, followed by drying. As the solvent, there can be used ketones such as acetone, methyl ethyl ketone, etc.; ethers such as tetrahydrofuran, etc.; aromatic compounds such as toluene, xylenes, etc.; halogenated hydrocarbons such as methylene chloride, carbon tetrachloride, etc.; alcohols such as methanol, ethanol, propanol, etc. As the coating method, there can be used conventional ones such as a spin coating method, a dip coating method, etc.

In the case of forming the charge generation layer and the charge transport layer, the above-mentioned methods can also be employed. In such a case, either the charge generation layer or the charge transport layer may be formed as an upper layer, or one charge generation layer may be sandwiched between two charge transport layers.

When the naphthalocyanine compound of the formula (I) is vacuum deposited, it is preferably to heat the naphthalocyanine compound in a high vacuum of $10^{-5}$ to $10^{-6}$ mm Hg. In the case of coating the naphthalocyanine compound by a spin coating method, it is preferable to use a coating solution obtained by dissolving the naphthalocyanine compound of the formula (I) in a halogenated solvent such as chloroform or an aprotic solvent such as toluene and to spin coat at a number of revolutions of 3000 to 7000 rpm. In the case of coating the naphthalocyanine compound by a dipping method, it is preferably to dip the electroconductive support in a coating solution obtained by dispersing the naphthalocyanine compound of the formula (I) in a polar solvent such as methanol, dimethylformamide, etc. by using a ball mill, ultrasonic wave, or the like.

If necessary, a protective layer may be formed in the same manner as described above for coating the photoconductive layer and drying it.

The electrophotographic plate of this invention may further contain a thin adhesive layer or barrier layer immediately on the electroconductive support, or a protective layer on the surface thereof.

This invention is explained in detail by way of the following Synthesis Examples for synthesizing the naphthalocyanine compounds of the formula (I) and Examples, in which all parts and percents are by weight unless otherwise specified.

Synthesis Example 1

(1) Synthesis of 2,3-dicyanonaphthalene

To 0.1 mole of tetrabromoxylene, 0.17 mole of fumaronitrile, 0.66 mole of sodium iodide and 400 ml of anhydrous dimethylformamide were added and heated with stirring at 70° to 80° C. for 7 hours. The reaction solution was added to 800 g of ice water. To the deposited precipitate, about 15 g of sodium hydrogen sulfite was added and allowed to stand overnight. After filtration by suction and drying, white 2,3-dicyano-naphthalene was obtained by recrystallization from chloroform/ethanol in yield of 80%.

(2) Synthesis of 1,3-diiminobenz(f)isoindoline

In 2.5 moles of 2,3-dicyanonaphthalene, 0.075 mole of sodium methoxide and 1 liter of methanol, an ammonia gas was flowed with a suitable flow rate for 40 minutes. Then, the reaction solution was refluxed with heating while flowing the ammonia gas for 4 hours. After cooling, the product was filtered, and recrystallized from a mixed solvent of methanol/ether to yield yellow 1,3-diiminobenz(f)isoindoline in 66% yield.

(3) Synthesis of Dichlorosilicon Naphthalocyanine 1,3-Diiminobenz(f)isoindoline in an amount of 3 millimoles, 4.8 millimoles of silicon tetrachloride, 2 ml of dried tri-n-butylamine and 4 ml of dried tetralin were refluxed with heating for about 2.5 hours. After cooling, 3 ml of methanol was added to the reaction solution, and allowed to stand. After filtering by suction and washing with methanol sufficiently, there was obtained dark green dichlorosilicon naphthalocyanine in 24% yield.

(4) Synthesis of Dihydroxysilicon Naphthalocyanine

To 0.71 millimole of dichlorosilicon naphthalocyanine, 20 ml of concentrated sulfuric acid was added and stirred at room temperature for 2 hours, followed by addition of 60 g of ice to the reaction solution. After filtering by suction and drying, the precipitate was placed in 60 ml of 25% ammonia water and refluxed with heating for 1 hour to give dihydroxysilicon naphthalocyanine quantitatively.

(5) Synthesis of Bis(trihexlsiloxy)silicon Naphthalocyanine

To 0.8 millimole of dihydroxysilicon naphthalocyanine, 8 millimoles of trihexylsilyl chloride and 70 ml of β-picoline were added and refluxed with heating for 1.5 hours. After filtering, the filtrate was added to a mixed solution of water/ethanol to deposit a precipitate. After filtering the precipitate, it was recrystallized from n-hexane to give a naphthalocyanine compound in 50% yield.

Synthesis Example 2

Bis(dimethylpropylsiloxy)silicon naphthalocyanine was synthesized in the same manner as described in Synthesis Example 1 except for using dimethylpropylsilyl chloride in place of trihexylsilyl chloride in the step (5).

Synthesis Example 3

Bis(triethylsiloxy)silicon naphthalocyanine was synthesized in the same manner as described in Synthesis Example 1 except for using triethylsilyl chloride in place of trihexylsilyl chloride in the step (5).

Synthesis Example 4

Bis(tripropylsiloxy)silicon naphthalocyanine was synthesized in the same manner as described in Synthesis Example 1 except for using tripropylsilyl chloride in place of trihexylsilyl chloride in the step (5).

Synthesis Example 5

Bis(tributylsiloxy)silicon naphthalocyanine was synthesized in the same manner as described in Synthesis Example 1 except for using tripropylsilyl chloride in place of trihexylsilyl chloride in the step (5).

Synthesis Example 6

Bis(dimethoxymethylsiloxy)silicon naphthalocyanine was synthesized in the same manner as described in Synthesis Example 1 except for using dimethoxymethylsilyl chloride in place of trihexlsilyl chloride in the step (5).

Synthesis Example 7

Bis(triethoxysiloxy)silicon naphthalocyanine was synthesized in the same manner as described in Synthesis Example 1 except for using triethoxysilyl chloride in place of trihexylsilyl chloride in the step (5).

Example 1

Bis(triethoxysiloxy)silicon naphthalocyanine obtained in Synthesis Example 1 and having two trihexylsiloxy groups as L in the formula (I) was subjected to vacuum deposition in a vacuum of $2 \times 10^{-5}$ mm Hg by a heating method to form a charge generation layer of 400 nm thick on an aluminum vapor deposition substrate.

A coating solution obtained by dissolving 5 g of 1-phenyl-3-(p-diethylaminostyryl)-5-(p-diethylaminophenyl) pyrazoline and 10 g of polycarbonate resin in 85 g of 1:1 mixed solvent of methylene chloride and 1,1,2-trichloroethane was coated on the charge generation layer formed on the substrate by a dip coating method and dried at 120° C. for 30 minutes to form a charge transport layer of 15 μm thick.

Using an electrostatic charging analyzer (mfd. by Kawaguchi Electric Works Co., Ltd.), the resulting electrophotographic plate was charged negatively by corona discharge at 5 kV. Then, by irradiating a light obtained by using a halogen lamp as an outer light source and changing to a monochromatic light by using a monochrometer (mfd. by RITSU OYOKOGAKU Co., Ltd.), the light decay of the surface potential of the electrophotographic plate was measured.

As a result, when a monochromatic light of 800 nm in the near infrared region was used, the half decay exposure amount (the product of a time required for making the potential retention rate ½ by the light intensity) was 20 mJ/m².

Examples 2 to 5

Each charge generation layer was formed by vacuum deposition of the naphthalocyanine compounds obtained in Synthesis Examples 2 to 5 having two dimethylpropylsiloxy groups, triethylsiloxy groups, tripropylsiloxy groups, and tributylsiloxy groups, respectively.

A coating solution obtained by dissolving 5 g of 1-phenyl-3-(p-diethylaminostyryl)-5-p-diethylamino-phenyl) pyrazoline and 10 g of polycarbonate resin in 85 g of 1:1 mixed solvent of methylene chloride and 1,1,2-trichloroethane was dip coated on the charge generation layer formed on the substrate and dried at 120° C. for 30 minutes to form a charge transport layer of 15 μm thick.

The thus produced electrophotographic plates were subjected to the same test as in Example 1 to measure the half decay exposure amount by using a monochromatic light of 800 nm in the near infrared region. The results are shown in Table 1.

TABLE 1

| Example No. | L in the formula (I) | Half decay exposure amount (mJ/m²) |
|---|---|---|
| 2 | Dimethylpropylsiloxy | 25 |
| 3 | Triethylsiloxy | 8 |
| 4 | Tripropylsiloxy | 10 |
| 5 | Tributylsiloxy | 17 |

Examples 6 to 10

Each charge generation layer was formed by vacuum deposition of the naphthalocyanine compounds obtained in Synthesis Examples 1 to 5 in the same manner as described in Examples 1 to 5.

A coating solution obtained by dissolving 5 g of p-diethylaminobenzaldehyde-diphenylhydrazone and 10 g of polycarbonate resin in 85 g of 1:1 mixed solvent of methylene chloride and 1,1,2-trichloroethane was dip coated on the charge generation layer formed on the substrate and dried at 120° C. for 30 minutes to form a charge transport layer of 15 μm thick.

The thus produced electrophotographic plates were subjected to the same test as in Example 1 to measure the half decay exposure amount by using a monochromatic light of 800 nm in the near infrared region. The results are shown in Table 2.

TABLE 2

| Example No. | L in the formula (I) | Half decay exposure amount (mJ/m²) |
|---|---|---|
| 6 | Trihexylsiloxy | 22 |
| 7 | Dimethylpropylsiloxy | 28 |

TABLE 2-continued

| Example No. | L in the formula (I) | Half decay exposure amount (mJ/m$^2$) |
|---|---|---|
| 8 | Triethylsiloxy | 10 |
| 9 | Tripropylsiloxy | 12 |
| 10 | Tributylsiloxy | 20 |

Examples 11 to 17

A mixed solution of 2.5 g of a naphthalocyanine compound as listed in Table 3, 5.0 g of a silicon resin (KR-255, a trade name mfd. by Shin-etsu Chemical Industry Co., Ltd.) (solid content 50%), and 92.5 g of methyl ethyl ketone was kneaded for 8 hours by using a ball mill (a pot mill having a diameter of about 10 cm mfd. by NIPPON KAGAKU TOGYO Co., Ltd.). The resulting pigment dispersion was coated on an aluminum plate (an electroconductive support of 100 mm×70 mm) using an applicator and dried at 90° C. for 15 minutes to form a charge generation layer of 1 μthick.

A coating solution obtained by dissolving 5 g of 1-phenyl-3-(p-diethylaminostyryl)-5-p-diethylaminophenyl)pyrazoline and 10 g of polycarbonate resin in 85 g of 1:1 mixed solvent of methylene chloride and 1,1,2-trichloroethane was dip coated on the charge generation layer on the substrate and dried at 120° C. for 30 minutes to form a charge transport layer of 15 μm thick.

The thus produced electrophotographic plates were subjected to the same test as in Example 1 to measure the half decay exposure amount by using a monochromatic light of 800 nm in the near infrared region. The results are shown in Table 3.

TABLE 3

| Example No. | L in the formula (I) | Half decay exposure amount (mJ/m$^2$) |
|---|---|---|
| 11 | Trihexylsiloxy | 35 |
| 12 | Dimethylpropylsiloxy | 40 |
| 13 | Triethylsiloxy | 18 |
| 14 | Tripropylsiloxy | 20 |
| 15 | Tributylsiloxy | 28 |
| 16 | Dimethoxymethylsiloxy | 25 |
| 17 | Triethoxysiloxy | 28 |

Comparative Example 1

An electrophotographic plate was produced in the same manner as described in Example 1 except for using a phthalocyanine compound of the formula:

wherein L is (C$_6$H$_{13}$)$_3$Si—O—, in place of the bis(trihexylsiloxy)silicon naphthalocyanine. The half decay exposure amount for the monochromatic light of 800 nm measured under the same conditions as in Example 1 was 3000 mJ/m$^2$, which value means that the sensitivity is remarkably worse compared with Example 1.

Comparative Example 2

An electrophotographic plate was produced in the same manner as described in Comparative Example 1 except for using p-diethylaminobenzaldehyde-diphenylhydrazone as a charge transport substance in place of 1-phenyl-3-(p-diethylaminostyryl)-5-(p-diethylaminophenyl)pyrazoline. The half decay exposure amount of the electrophotographic plate using the monochromatic light of 800 nm in the near infrared region measured in the same manner as described in Example 1 was 3200 mJ/m$^2$.

Reference Example

Each solution was prepared by dissolving a phthalocyanine wherein two trihexylsiloxy groups were bonded to the central metal silicon or a naphthalocyanine compound wherein two trihexylsiloxy groups were bonded to the central metal silicon (the naphthalocyanine compound synthesized in Synthesis Example 1) in chloroform to measure an absorption spectrum. The results are shown in FIG. 1.

Figure 1:
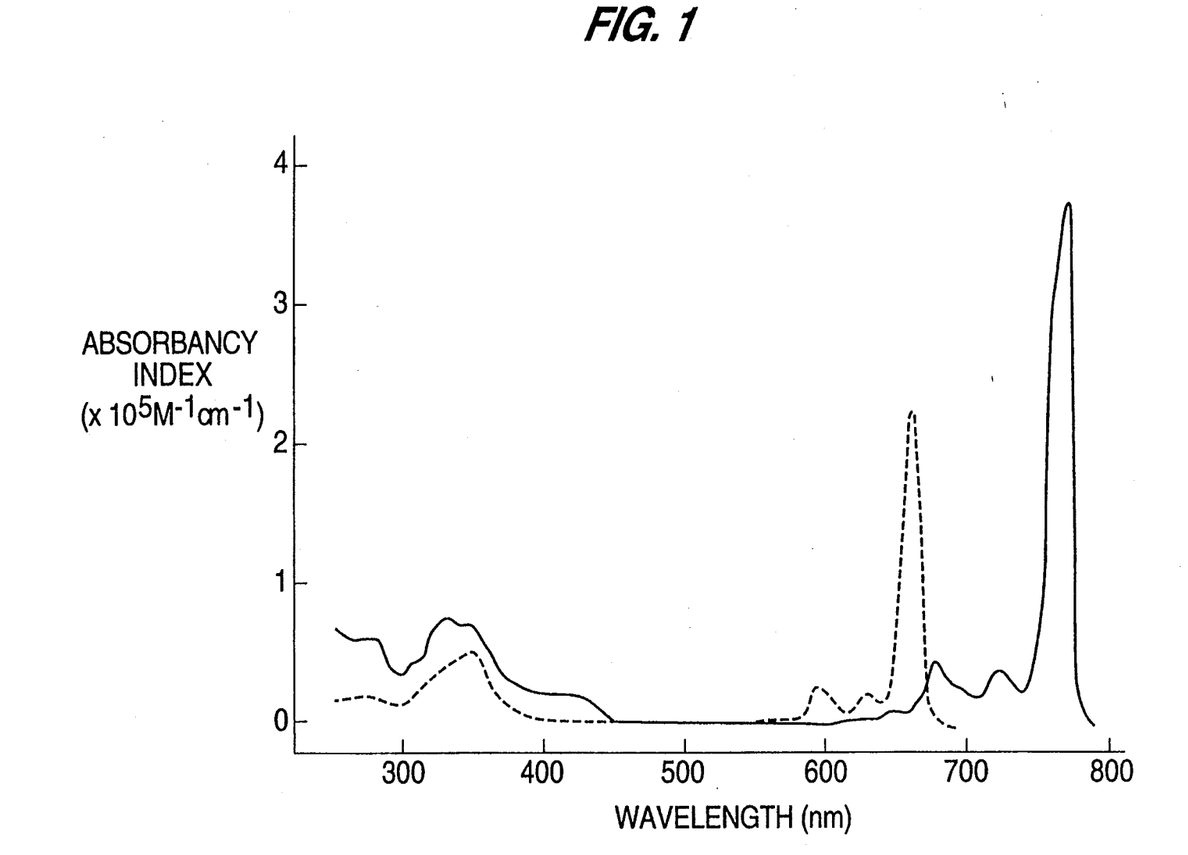
FIG. 1 is absorption spectra of a naphthalocyanine having two trihexylsiloxy groups bonded to the central metal silicon synthesized in Synthesis Example 1 (solid line), and a phthalocyanine similar to it (dotted line).

As is clear from FIG. 1, the phthalocyanine (the dotted line) shows absorptions only in the region of 700 nm or less, whereas the naphthalocyanine (the solid line) shows an absorption at near 800 nm.

Figure 2:
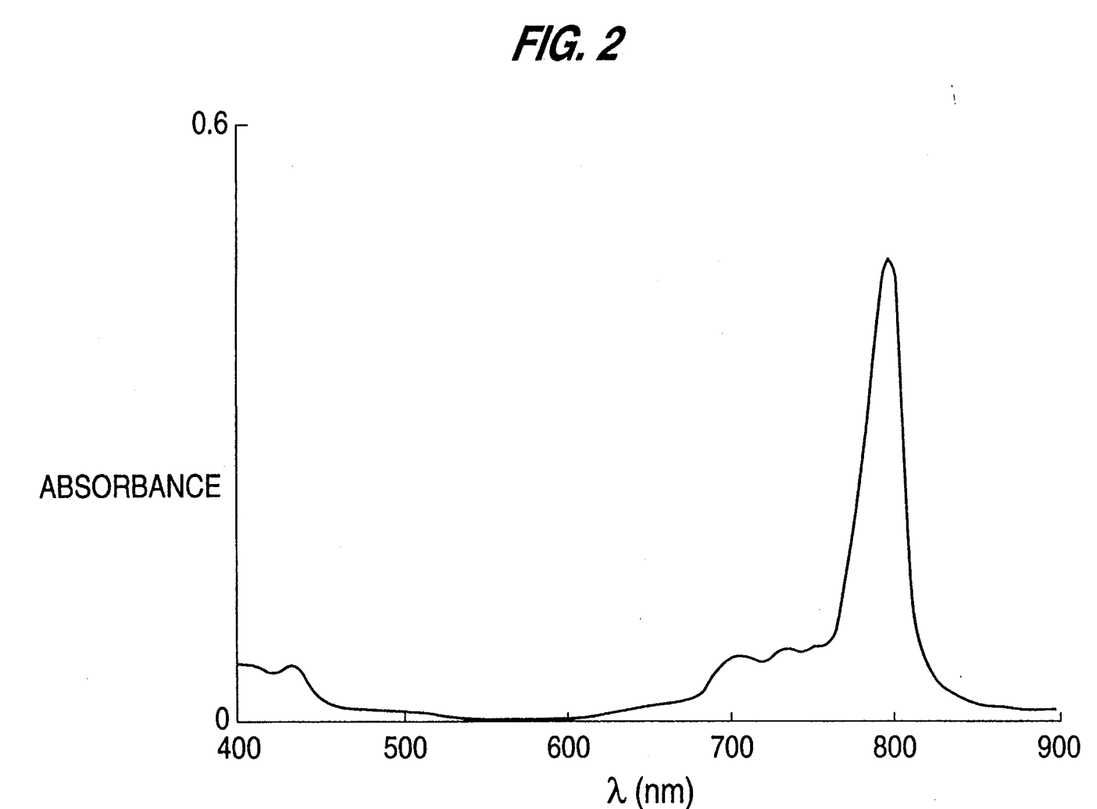
FIG. 2 is an absorption spectrum of a vapor deposited film of naphthalocyanine having two trihexylsiloxy groups bonded to the central metal silicon synthesized in Synthesis Example 1.

FIG. 2 shows an absorption spectrum of a vacuum deposited film of the above-mentioned naphthalocyanine. In this case, the absorption is shown at 800 nm.

As mentioned above, the electrophotographic plate of this invention shows a large absorption at near 800 nm and has properties of showing high sensitivity for the longer wavelength region. Thus, when it is used in a diode laser beam printer, excellent effects are exhibited. Further, the electrophotographic plate of this invention can be used not only for the diode laser beam printer as mentioned above but also for FAX (facsimile telegraphy) or a printer using LED as a light source, and other light recording devices using a diode laser as a light source.

Example 18

To a suspension of 35 ml of quinoline containing 774 mg (1 mmol) of dihydroxynaphthalocyanine, 3.5 ml (23 mmol)) of triethylsilanol was added and refluxed for about 3 hours. After cooling, the reaction mixture was poured into 200 ml of ethanol/water (1/1), stirred well and allowed to stand overnight. A deposited precipitate was filtered and washed with methanol. A soluble portion of the precipitate was dissolved with about 6000 ml of hot chloroform and the resulting chloroform solution was concentrated to about 50 ml. After cooling the concentrated chloroform solution, deposited crystals were filtered and washed with chloroform. The obtained crystals were recrystallized from chloroform to give 3600 mg of dark green crystals in 36% yield. The dark green crystals were identified as bis(tri-ethylsiloxy)silicon naphthalocyalanine [L is —O—Si—(—C$_2$H$_5$)$_3$ in the formula (I)] by the following analytical results.

(1) Melting point: >300° C.
(2) Elementary analysis:

| | C (%) | H (%) | N (%) |
|---|---|---|---|
| Calcd. | 71.82 | 3.42 | 11.17 |

| | C (%) | H (%) | N (%) |
|---|---|---|---|
| Found | 70.45 | 5.34 | 10.92 |

Figure 3:
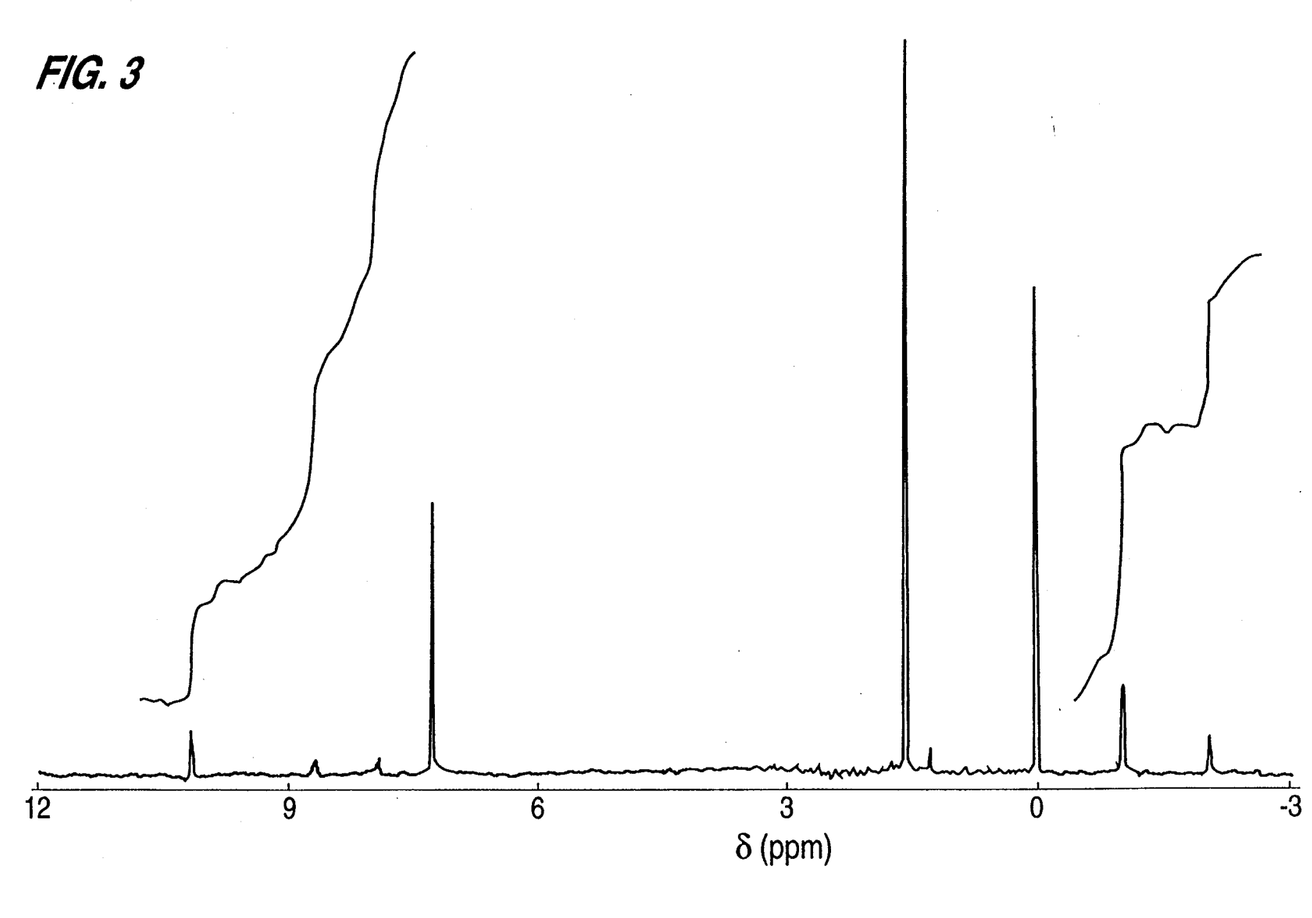
FIG. 3 is an NMR spectrum of bis(triethylsiloxy)silicon naphthalocyanine.

(3) NMR values (CDCl₃ solvent, FIG. 3) δ values 10.13 (8H, s) 8.68 (8H, dd, J=6.10, 3.05 Hz) 7.93 (8H, dd, J=6.10, 3.05 Hz) −1.02 (12H, t, J=7.93 Hz) −2.07 (18H, q, J=7.93 Hz)

Figure 4:
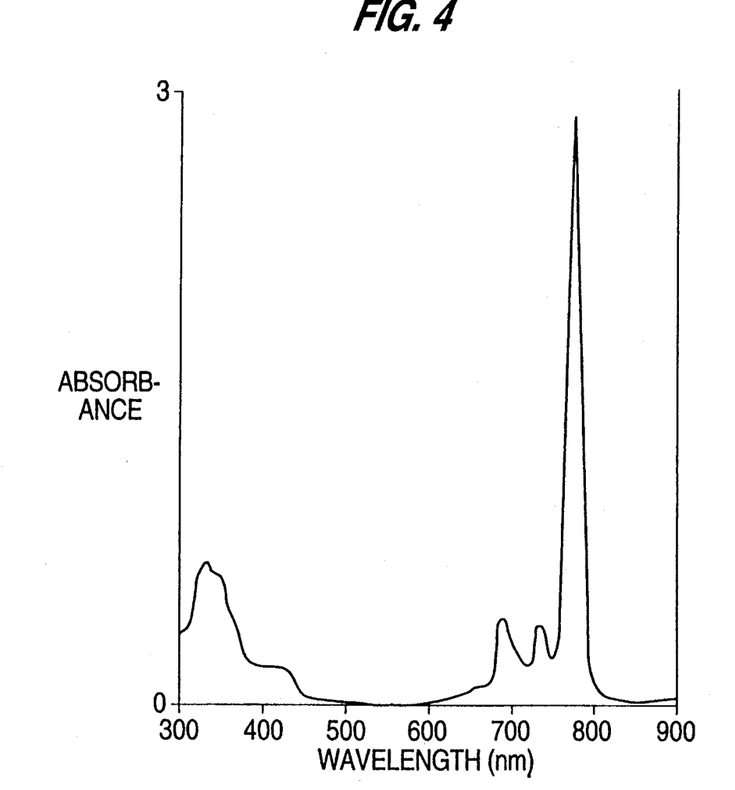
FIG. 4 is a UV spectrum of bis(triethylsiloxy)silicon naphthalocyanine.

(4) UV spectrum (CHCl₃ solution): FIG. 4

Example 19

To 420 ml of a suspension of anhydrous β-picoline containing 3 g (3.9 mmol) of dihydroxysilicon naphthalocyanine, 12 ml (50.4 mmol) of anhydrous tri-n-butylamine and then 13.2 ml (49.2 mmol) of tri-n-butylchlorosilane were added in a nitrogen atmosphere and refluxed for about 2 hours. After cooling, the resulting mixture was poured into 600 ml of ethanol/water (1/1), stirred well and allowed to stand overnight. A deposited precipitate was filtered and washed with water. A soluble portion of the precipitate was dissolved with about 600 ml of hot chloroform and the chloroform solution was dried over anhydrous sodium sulfate, followed by concentration to about 50 ml. After cooling the concentrated chloroform solution, deposited crystals were filtered and washed with chloroform. The mother liquid was concentrated and eluted by using benzene as a developing solvent by means of alumina column chromatography. Then the green benzene solution was concentrated and added with hexane to deposit crystals, which were filtered and washed with hexane sufficiently. All the obtained crude crystals were recrystallized from chloroform to give about 2 g (44% yield) of dark green crystals. The dark green crystals were identified as bis(tri-n-butylsiloxy)silicon naphthalocyanine by the following analytical results.

(1) Melting point: >300° C.

(2) Elementary analysis:

| | C (%) | H (%) | N (%) |
|---|---|---|---|
| Calcd. | 73.01 | 6.71 | 9.50 |
| Found | 73.71 | 6.73 | 9.40 |

Figure 5:
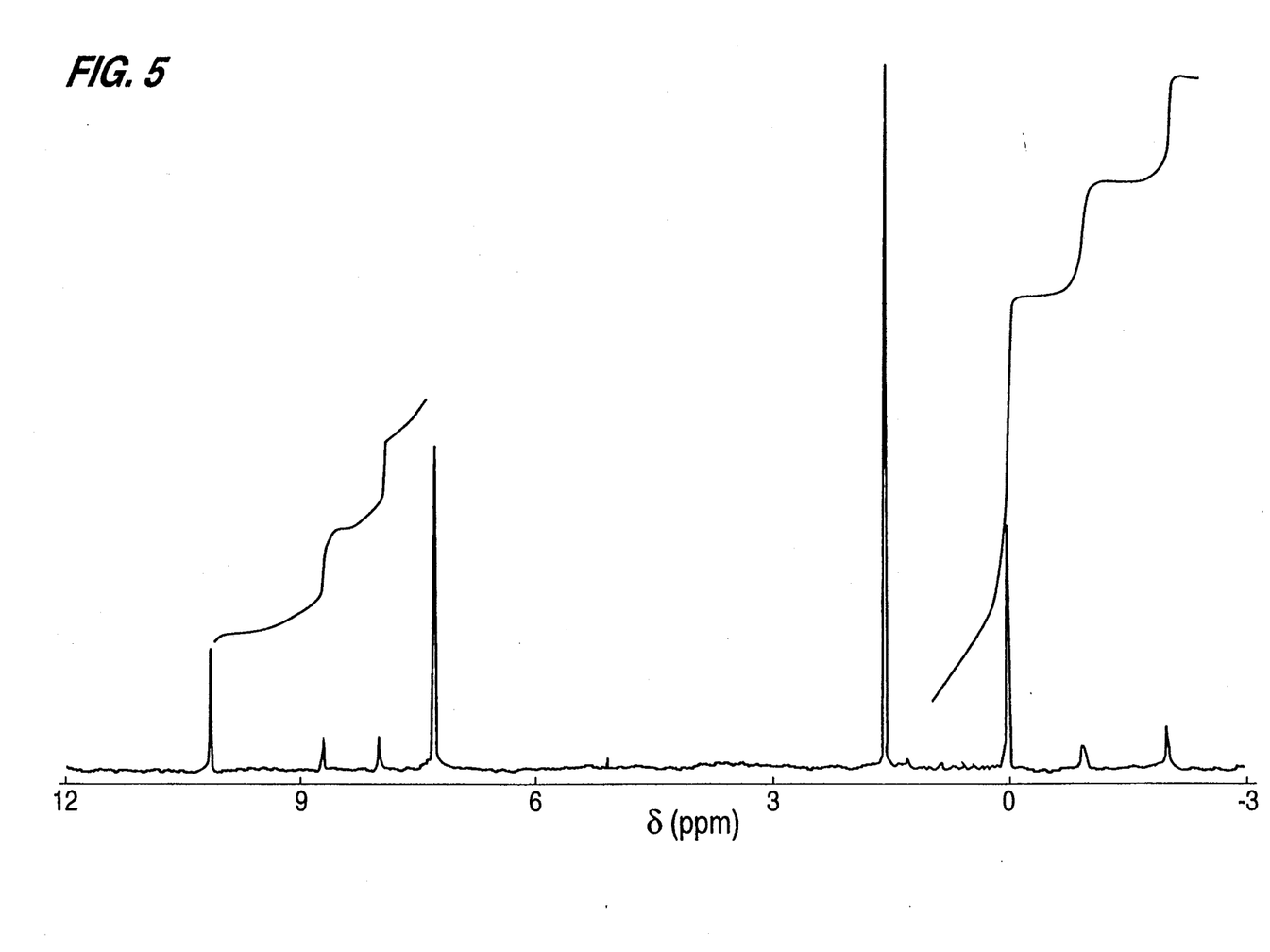
FIG. 5 is an NMR spectrum of bis(tri-n-butylsiloxy)silicon naphthalocyanine.

(3) NMR values (CDCl₃, FIG. 5) δ values 10.11 (8H, s) 8.67 (8H, dd, J=6.10, 3.35 Hz) 7.92 (8H, dd, J=6.10, 3.35 Hz) −0.1 to 0.1 (30H, m) −0.97 (12H, quintet, J=7.32 Hz) −2.07 (12H, t, J=7.32 Hz)

Figure 6:
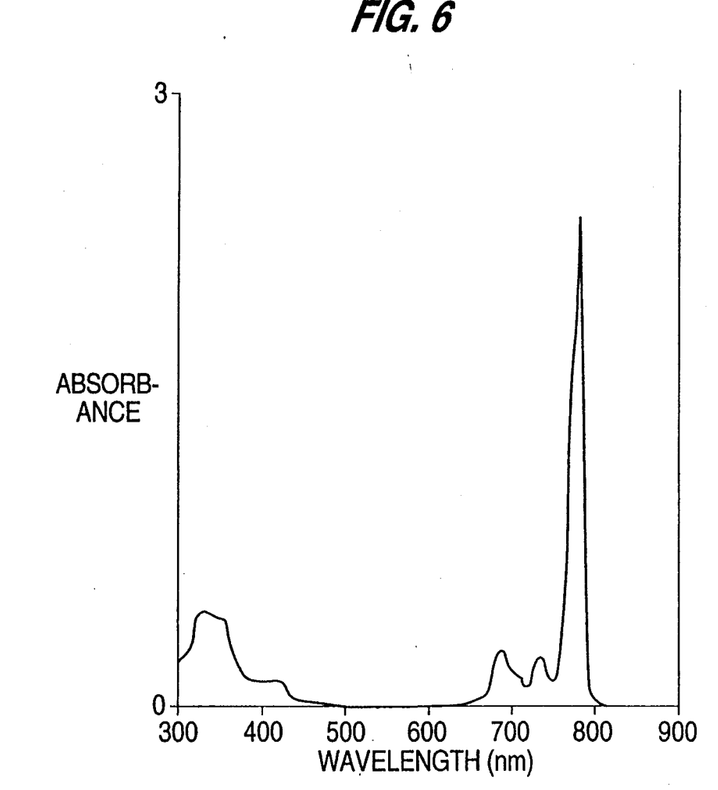
FIG. 6 is a UV spectrum of bis(tri-n-butylsiloxy)silicon naphthalocyanine.

(4) UV spectrum (CHCl₃ solution): FIG. 6

Example 20

To 420 ml of a suspension of anhydrous β-picoline containing 3 g (3.9 mmol) of dihydroxysilicon naphthalocyanine, 12 ml (50.4 mmol) of anhydrous tri-n-butylamine and then 10.8 ml (49.2 mmol) of tri-n-propylchlorosilane were added and refluxed for about 2 hours. After cooling, the reaction mixture was treated in the same manner as described in Example 19 and the recrystallization was carried out using chloroform. As a result, 1.45 g (34% yield) of dark green crystals were obtained. The dark green crystals were identified as bis(tri-n-propylsiloxy)-silicon naphthalocyanine by the following analytical results.

(1) Melting point: >300° C.

(2) Elementary analysis:

| | C (%) | H (%) | N (%) |
|---|---|---|---|
| Calcd. | 72.89 | 6.12 | 10.30 |
| Found | 72.70 | 6.13 | 10.28 |

Figure 7:
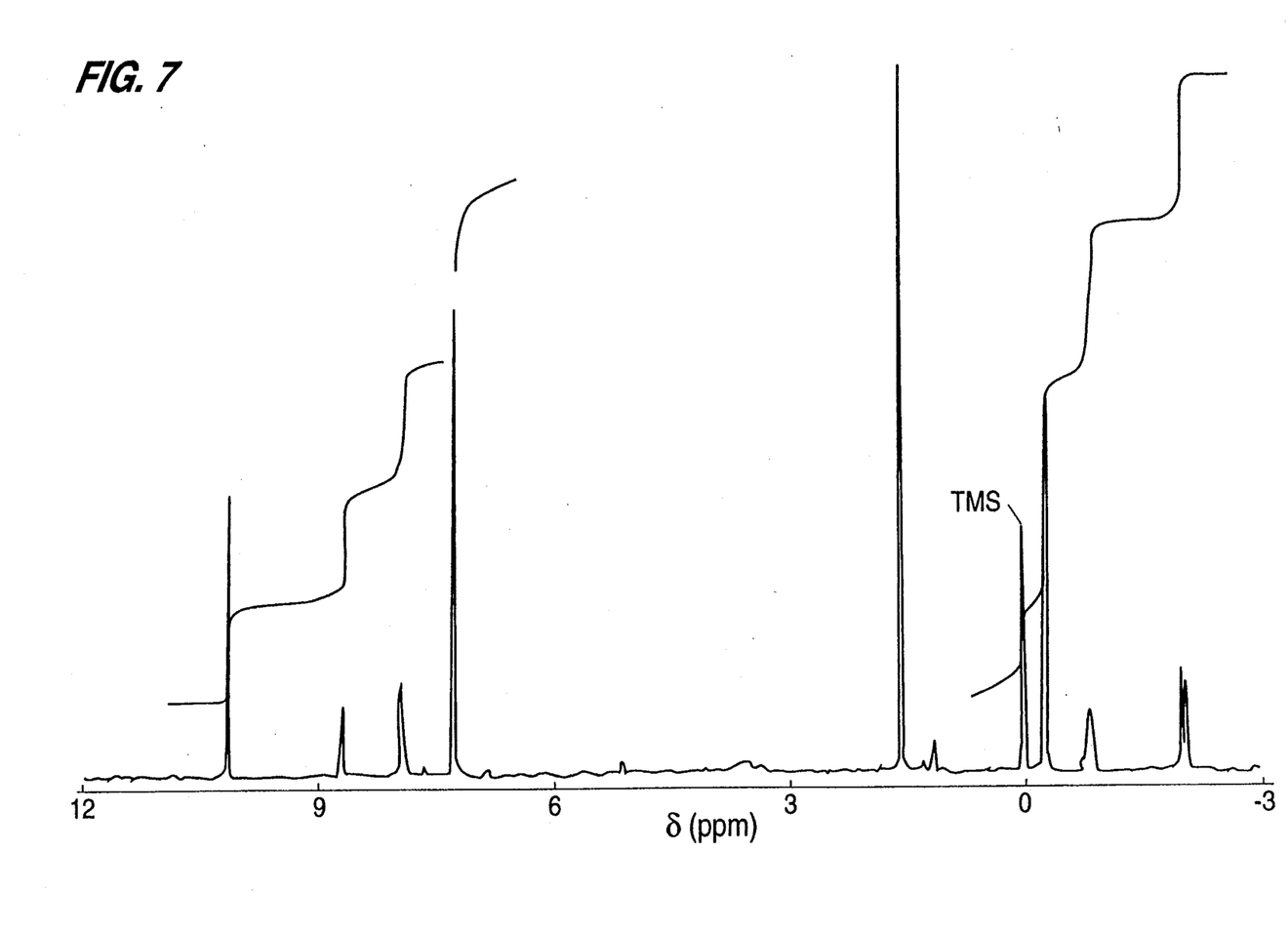
FIG. 7 is an NMR spectrum of bis(tri-n-propylsiloxy)silicon naphthalocyanine.

(3) NMR values (CDCl, FIG. 7) values 10.03 (8H, s) 8.68 (8H, dd, J=6.10, 3.03 Hz) 7.93 (8H, dd, J=6.10, 3.03 Hz) −0.28 (18H, t, J=7.32 Hz) −0.85 (12H, sextet, J=7.32 Hz) −2.06 (12H, t, J=7.32 Hz)

Figure 8:
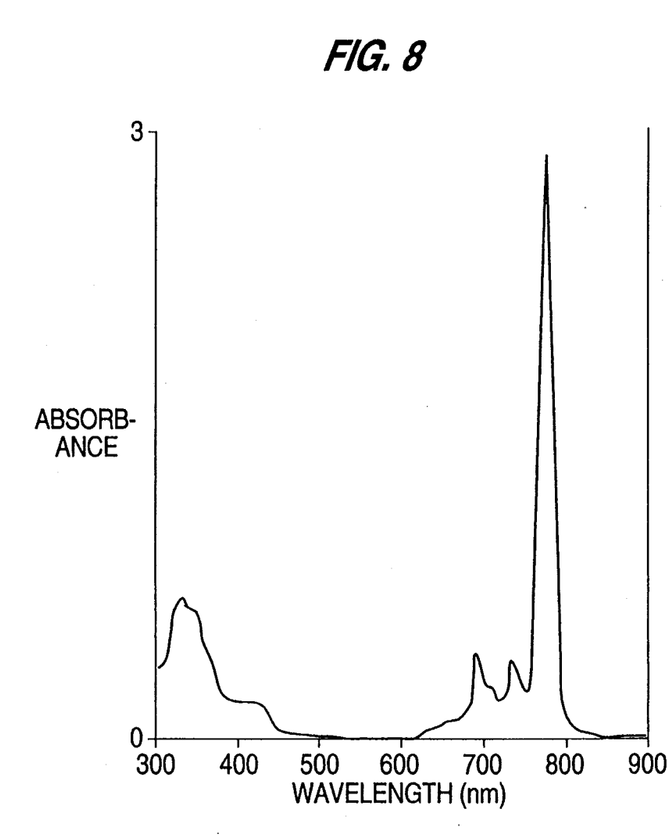
FIG. 8 is a UV spectrum of bis(tri-n-propylsiloxy)silicon naphthalocyanine.

(4) UV spectrum (CHCl₃ solution): FIG. 8

Example 21

Figure 9:
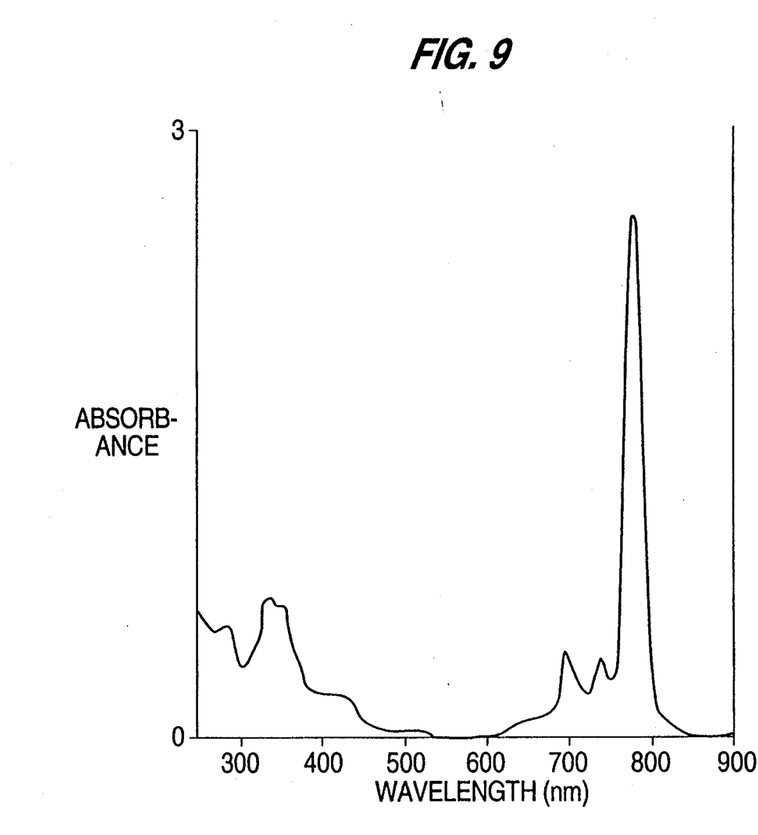
FIG. 9 is a UV spectrum of bis(trimethylsiloxy)silicon naphthalocyanine.

To 140 ml of a suspension of anhydrous β-picoline containing 1 g (1.3 mmol) of dihydroxysilicon naphthalocyanine, 4 ml (16.8 mmol) of anhydrous tri-n-butylamine and then 2.1 ml (16.4 mmol) of trimethylchlorosilane were added and refluxed for about 2 hours. After cooling, the reaction mixture was treated in the same manner as described in Example 19 to give dark green crystals of bis(trimethylsiloxy)silicon naphthalocyanine. FIG. 9 shows a UV spectrum of this compound (CHCl₃ solution).

What is claimed is:

1. A bis(trialkylsiloxy)silicon naphthalocyanine represented by the formula:

(I)

wherein L is a group of the formula: R₁R₂R₃Si—O—; and R₁, R₂ and R₃ are each a same alkyl group having 1 to 3 carbon atoms.

2. A bis(trialkylsiloxy)silicon naphthalocyanine according to claim 1, wherein the naphthalocyanine has sufficient sensitivity to long wavelength light of about 800 nm such that the naphthalocyanine can act as a charge generating material of a photoconductive layer for an electrophotographic plate using a light source with a wavelength of about 800 nm.

3. A bis(trialkylsiloxy)silicon naphthalocyanine according to claim 1, wherein each of R₁, R₂ and R₃ is an ethyl group.

4. A bis(trialkylsiloxy)silicon naphthalocyanine according to claim 1, wherein each of R₁, R₂ and R₃ is a propyl group.

5. A bis(trialkylsiloxy)silicon naphthalocyanine according to claim 1, wherein each of R₁, R₂ and R₃ is a methyl group.

* * * * *